United States Patent [19]

Mössle et al.

[11] 4,403,957

[45] Sep. 13, 1983

[54] DENTAL HANDPIECE HAVING OWN ELECTRICAL LIGHT SOURCE

[75] Inventors: Walter Mössle, Bad Waldsee; Bernhard Lingenhole; Eugen Eibofner, both of Biberach, all of Fed. Rep. of Germany

[73] Assignee: Kaltenbach & Voigt GmbH & Co., Biberach an der Riss, Fed. Rep. of Germany

[21] Appl. No.: 375,766

[22] Filed: May 6, 1982

[30] Foreign Application Priority Data

May 18, 1981 [DE] Fed. Rep. of Germany ....... 3119689

[51] Int. Cl.³ .......................... A61C 1/00; A61C 3/00
[52] U.S. Cl. ........................................................ 433/29
[58] Field of Search ............................. 433/29, 100, 99

[56] References Cited

U.S. PATENT DOCUMENTS 4,330,274  5/1982  Friedman et al. ..................... 433/29

FOREIGN PATENT DOCUMENTS 15659  9/1980  European Pat. Off. .............. 433/29

Primary Examiner—Robert Peshock
Attorney, Agent, or Firm—Scully, Scott, Murphy & Presser

[57] ABSTRACT

A dental handpiece having a gripping sleeve, a drive aggregate arranged in the handpiece for a dental treatment work tool retained in a head portion, and which includes its own built-in electrical light source. The light source, together with conduits for supply media, is arranged within an intermediate member which is exchangeably mounted between the gripping sleeve and the end member of a supply hose for the media for the handpiece. The light from the light source, with the aid of strand-like light conductors arranged interiorly of the handpiece, is conducted to the region of the handpiece head portion and exits therefrom the gripping sleeve directed towards the tooth treatment worktool, and in which the light source can be switched on and off through the intermediary of a compressed air-driven pneumatic switch device.

18 Claims, 27 Drawing Figures

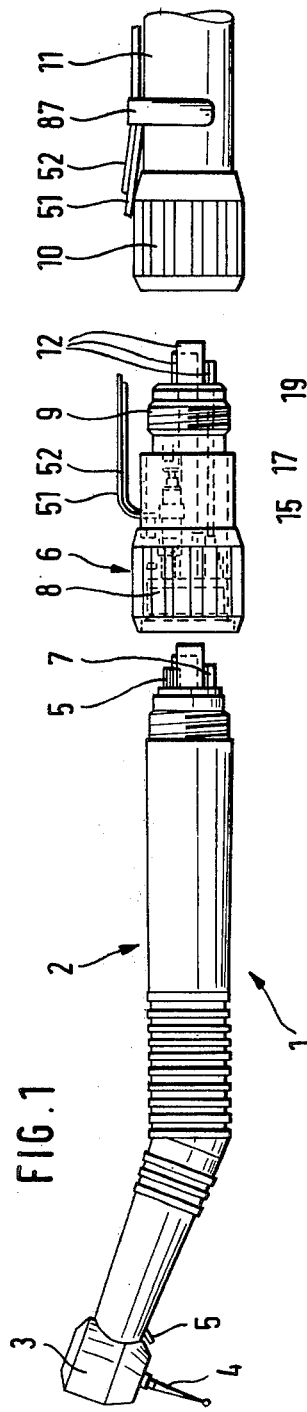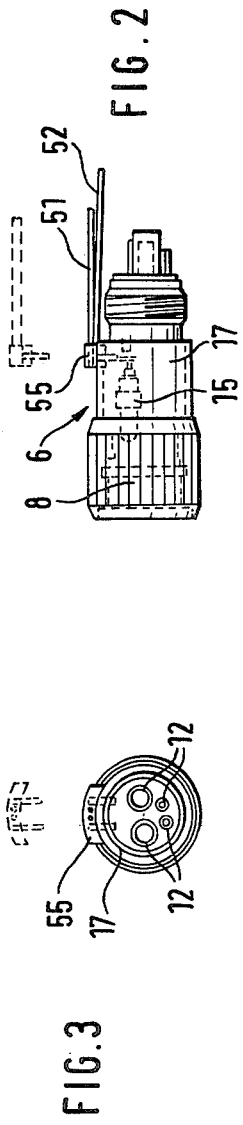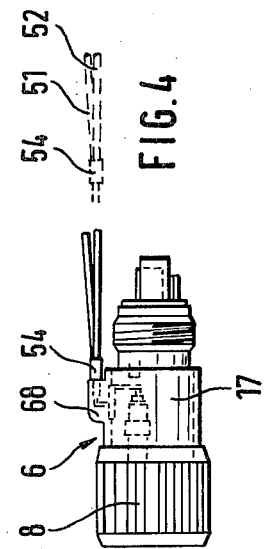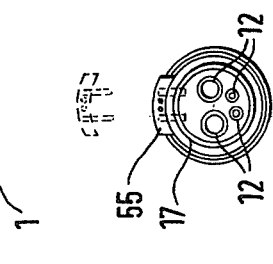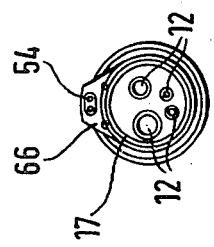

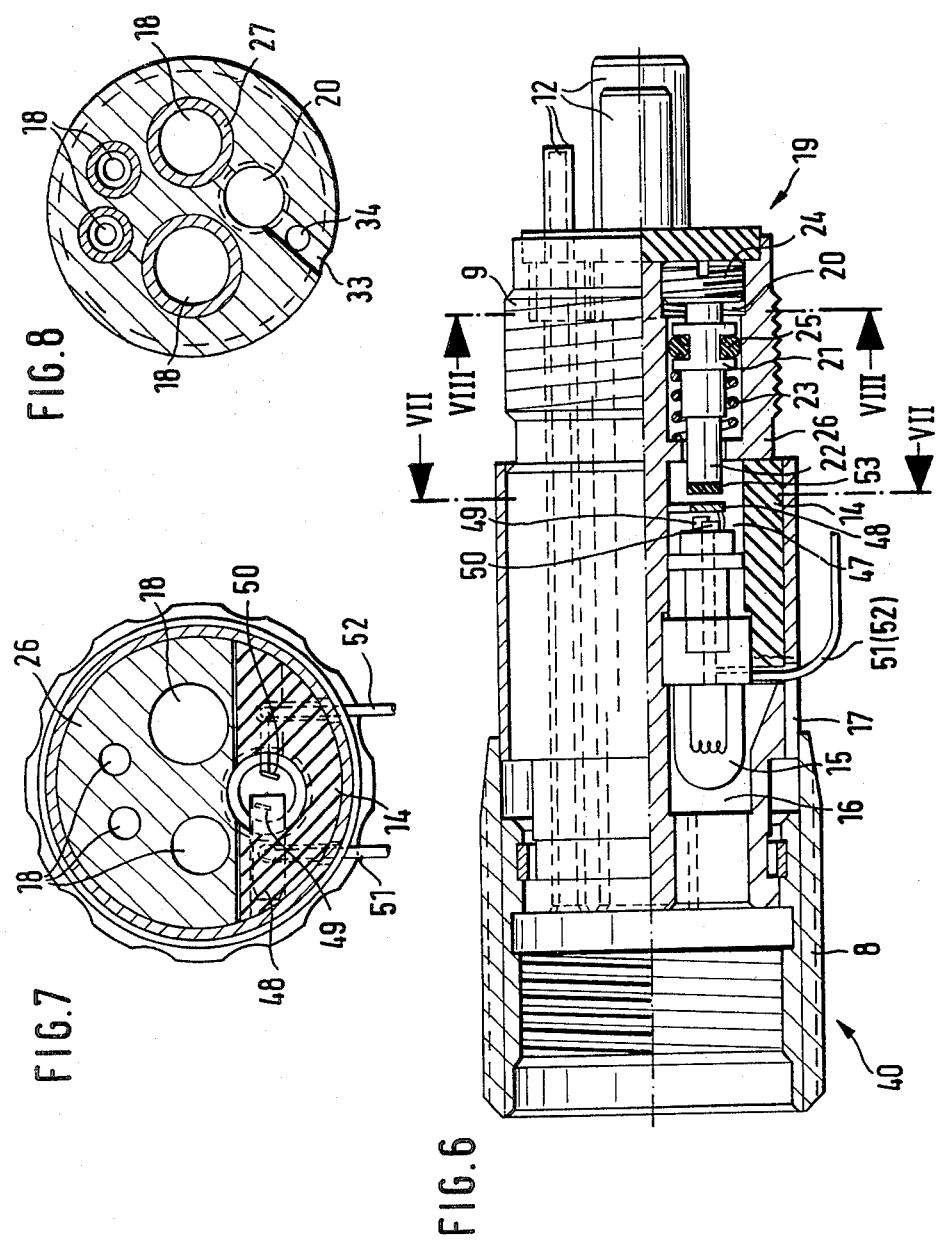

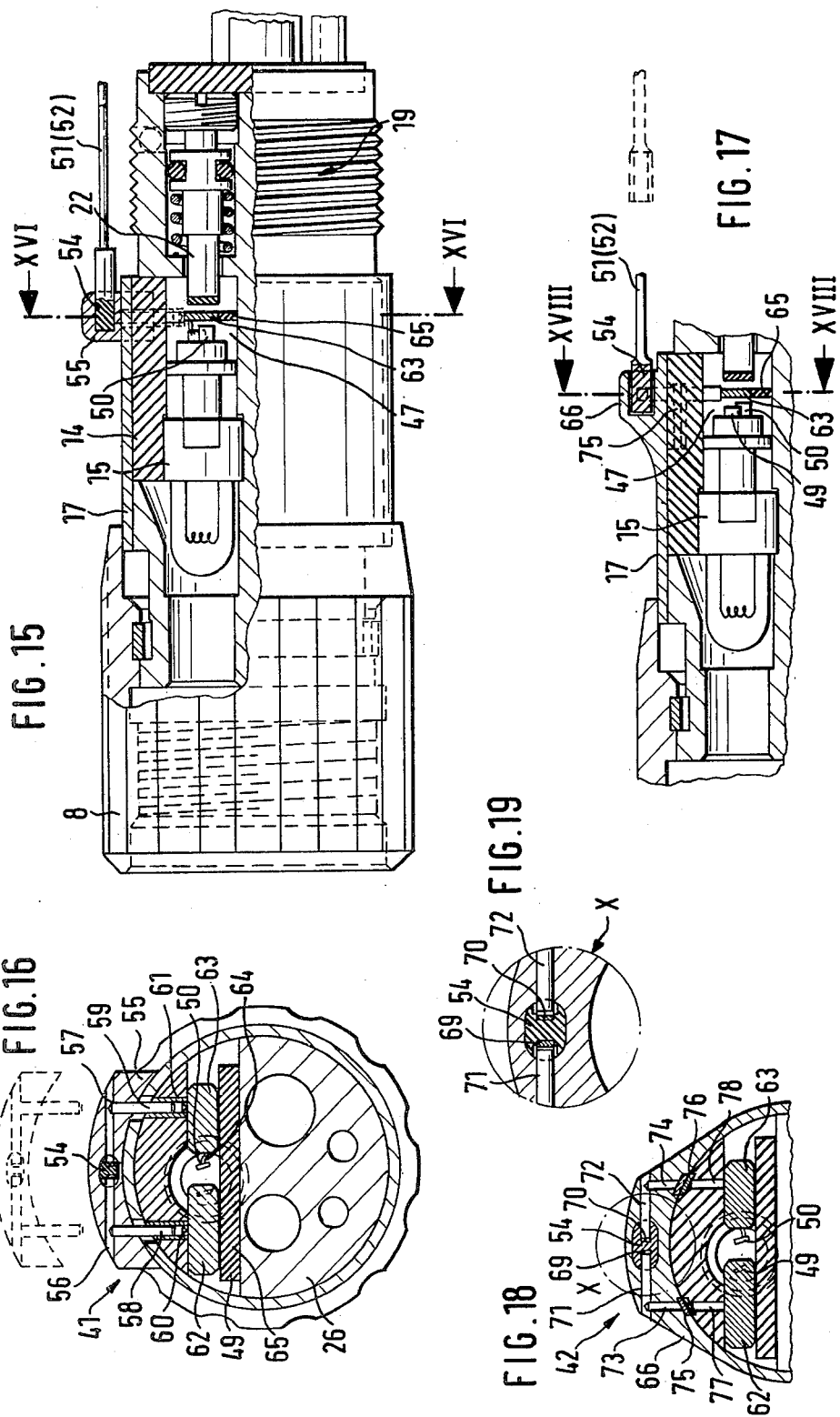

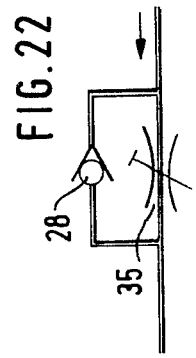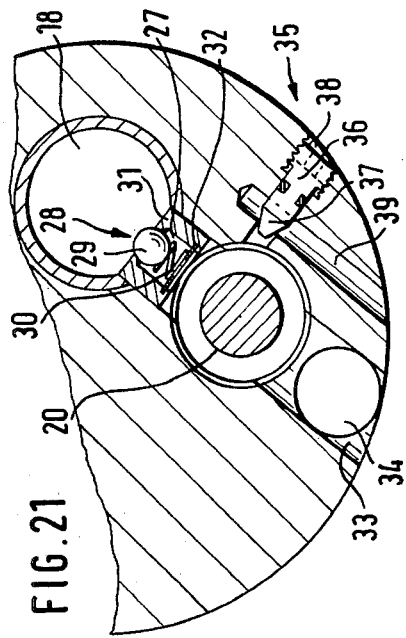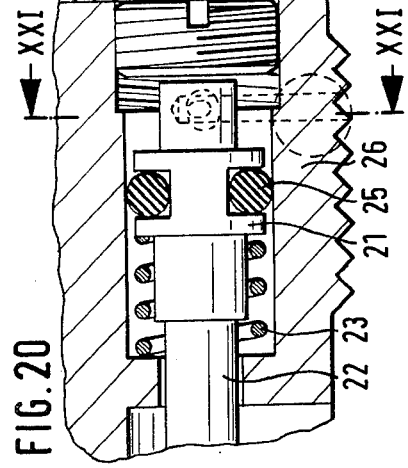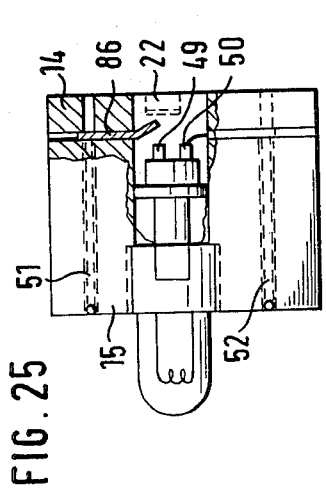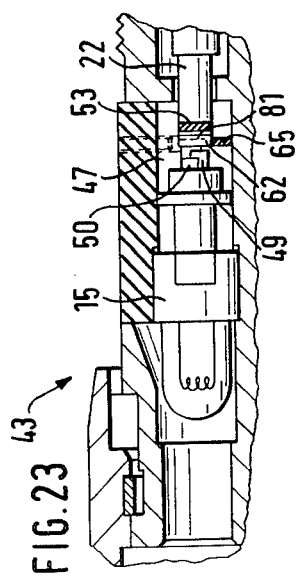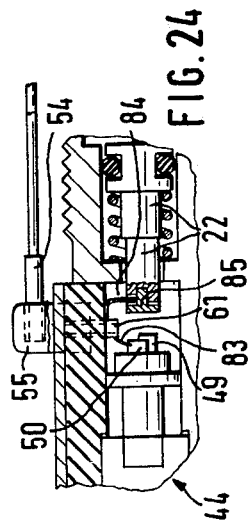

DENTAL HANDPIECE HAVING OWN ELECTRICAL LIGHT SOURCE

BACKGROUND OF THE INVENTION

1. Field of the Invention

The present invention relates to a dental handpiece having a gripping sleeve, a drive aggregate arranged in the handpiece for a dental treatment work tool retained in a head portion, and which includes its own built-in electrical light source. The light source, together with conduits for supply media, is arranged within an intermediate member which is exchangeably mounted between the gripping sleeve and the end member of a supply hose for the supply media for the handpiece The light from the light source, with the aid of strand-like light conductors arranged interiorly of the handpiece, is conducted to the region of the handpiece head portion and exits there from the gripping sleeve directed towards the tooth treatment worktool, and in which the light source can be switched on and off through the intermediary of a compressed air-driven pneumatic switch device.

2. Discussion of the Prior Art

A dental handpiece of that type has become known from the sales brochure HP013-879-2011 issued by the firm Midwest American. In order to change over a dental treatment unit, whose handpieces are normally not provided with its own built-in light source of the above mentioned type, into a unit in which a light source is built into the handpiece, it has been found to be necessary to exchange the collective connections on the handpiece and the entire supply hose. However, inasmuch as a large number of handpiece connector couplings and supply hoses are present which are differently constructed and are of different lengths, such a changeover causes considerable problems. Moreover, frequently there must be provided an additional suitable connection for the electrical conduits. In addition, above all there must also always be considered that for possibly occuring defects or disturbances in the light installation due to the separate arrangement of the intermediate member and the pneumatic switch device, inspections must be conducted at a number of locations, which renders the overcoming of this drawback quite complex and time-consuming.

Furthermore, disclosed in U.S. Pat. No. 3,634,938 is a similar dental handpiece in which there is also arranged between the gripping sleeve and the end body of the supply hose, an interchangeable intermediate member which contains the light source. This intermediate member always evidences a diameter which is large in comparison with the gripping sleeve, and which is quite unwieldly with respect to the manipulation of the handpiece, since at its end surfaces there are provided the connections for the strand-like light conductor, which projects at least partially outwardly of the gripping sleeve and which are provided for the electrical conduit for the light source. Moreover, required for this electrical conduit is a separate cable which leads to a transformer located remote from the handpiece and which, in turn, has a hand-operated switch connected ahead thereof in the power supply.

In a handpiece of that kind it is also relatively easy to construct the intermediate member with the light source in order to place it into operation; however, this large sized intermediate member, during manipulation of the handpiece, is disturbingly located in the crook between the thumb and the index finger. Moreover, in placing the handpiece into operation, the lighting installation of the handpiece must be switched on by means of a separate handswitch, which is cumbersome. The primary disadvantage lies in that also in this known handpiece, for possible disruptions in the light installation, inspections must be undertaken at a number of locations, which is extremely time consuming.

SUMMARY OF THE INVENTION

Accordingly, it is an object of the present invention to provide a dental handpiece of the above mentioned type in which, during the changing over of a dental treatment unit in the above-described manner, there need not be undertaken on the handpiece itself nor on the supply hose any modifications or built-in additions. Hereby, there should be ensured that dental handpieces can be utilized with and without built-in light sources with the one and the same usual supply hose and its connecting member. However, above all, the investigation for sources of error in the lighting installation and its elimination should be rendered considerably easier.

The advantages which are achieved through the present invention can be essentially ascertained in that with the utilization of an intermediate member which contains the light source as well as its pneumatic switching installation, and wherein the intermediate member is arranged between the gripping sleeve and the end member of the supply hose, there is created a relatively small and compact modular unit, which can be easily removed and disassembled, and which contains all of those components in which there can occur defects and disruptions in the lighting installation. When the intermediate member is removed, then it can be examined and, if required, repaired while, concurrently, the gripping sleeve with the supply hose can be directly interconnected so that in the interim there can be operated with the handpiece, although without its own light source, or the intermediate member can simply be exchanged.

Further advantageous modifications and features of the invention may be ascertained from the detailed description of the invention as set forth hereinbelow.

BRIEF DESCRIPTION OF THE DRAWINGS

Reference may now be had to the following detailed description of exemplary embodiments of the invention, taken in conjunction with the accompanying drawings; in which:

FIG. 1 illustrates a side view of a first embodiment of the dental handpiece, generally shown in its actual size, with the intermediate member for the lighting installation and with the connector portion of the supply hose shown in a pulled apart condition;

FIG. 2 illustrates a side view of the intermediate section in an embodiment which is modified with respect to that of FIG. 1;

FIG. 3 illustrates a right-hand end view of the intermediate member according to FIG. 2;

FIG. 4 illustrates a side view of the intermediate member in an embodiment modified with respect to that of FIGS. 1 and 2;

FIG. 5 illustrates a right-hand end view of the intermediate member according to FIG. 4;

FIG. 6 illustrates a partially sectional side view of the intermediate member pursuant to FIG. 1 in an enlarged scale, with a first embodiment of the connecting wire guidance and the connector contacts thereof;

FIG. 7 illustrates a section taken along line VII—VII in FIG. 6;

FIG. 8 illustrates a section taken along line VIII—VIII in FIG. 6;

FIG. 15 illustrates, in an enlarged scale, a partially sectional side view of the intermediate member accordinng to FIG. 2, with a second embodiment of the connecting wire guidance and the connector contacts;

FIG. 16 illustrates a section taken along line XVI—XVI in FIG. 15;

FIG. 17 illustrates, partially in section and in an enlarged scale, the intermediate member according to FIG. 3, with a third embodiment of the connecting wire guidance and the connector contacts;

FIG. 18 illustrates a section taken along line XVII—XVII in FIG. 17;

FIG. 19 illustrates, in an enlarged scale, a detail of the reinforced closure sleeve as shown in the portion marked "X" in FIG. 18;

FIG. 20 illustrates an enlarged scale section of a detail of the pneumatic switching device for the electrical lightbulb;

FIG. 21 illustrates a section taken along line XXI—XXI in FIG. 20;

FIG. 22 illustrates a schematic representation of the venting arrangement for the pneumatic switch device;

FIG. 23 illustrates, in an enlarged scale, a detail of a fourth embodiment of the connecting wire guidance and a connector contacts located in the intermediate member;

FIG. 24 illustrates, in an enlarged scale, a detail of a fifth embodiment of the connecting wire guidance and connector wire contacts arranged in the intermediate member;

FIG. 25 illustrates, in an enlarged scale, a sixth embodiment of a detail of the connecting wire guidance and the connector contacts in the intermediate member;

DETAILED DESCRIPTION

Figure 10:
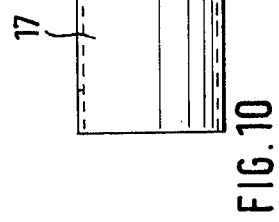
FIG. 10 illustrates the sleeve which is slidable over the central recess of the intermediate member pursuant to FIG. 9.
Figure 13:
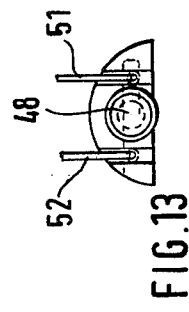
FIG. 13 illustrates a left-hand end view of the socket pursuant to FIG. 11.
Figure 14:
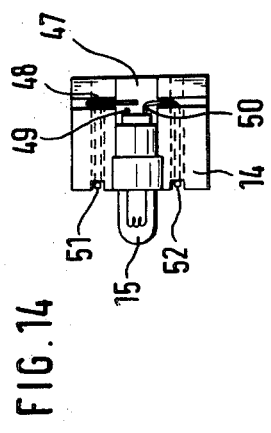
FIG. 14 illustrates a bottom view of the socket pursuant to FIG. 11.
Figure 11:
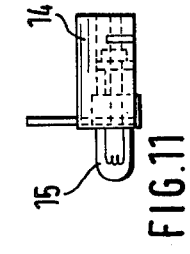
FIG. 11 illustrates a side view of the socket which is insertable into the central recess of the intermediate member pursuant to FIG. 9, together with the electrical connecting wires and contacts of the embodiment pursuant to FIGS. 1 and 6.

The dental handpiece 1, which is illustrated in FIG. 1 in a pulled-apart condition, consists of a gripping sleeve 2 which includes at its foward end, for example, compressed air-driven drive aggregate in a head portion 3. This drive aggregate can be constructed as an electric motor, an air motor or as an air turbine, into a hollow rotor shaft of which there can be inserted a dental treatment worktool 4. Arranged within the gripping sleeve 2 along its entire length axially adjacent the media flow passageways (not shown) is a strand-shaped light conductor 5 which, for example, can be formed from a bundle of light-conductive fibers, and which exits from the gripping sleeve 2 at the connecting location between the gripping sleeve 2 and the headpiece 3 in such a manner that the light beam which emanates from the light conductor 5 is projected onto the surfaces of the working dental treatment worktool 4 or, in essence, onto the location of the tooth which is to be treated.

From the illustration in FIG. 1 there can be ascertained that, at the end of the gripping sleeve 2 which is remote from the worktool, there can be attached a cylindrical intermediate member 6 with the aid of sleeves (not shown) onto the inlet connectors 7 of the gripping sleeve 2 and secured in position by means of a cap screw 8. The rearward end of the intermediate member 6 is provided with an external thread 9 onto which there can be screwed the end member 10 of the supply hose 11 in such a manner that the media inlet connectors 12 of the intermediate member 6 can be slid into sleeves (not shown) of the end member 10. The outer diameter of the intermediate member 6 is approximately equal to that of the rearward portion of the gripping sleeve 2.

Figure 9:
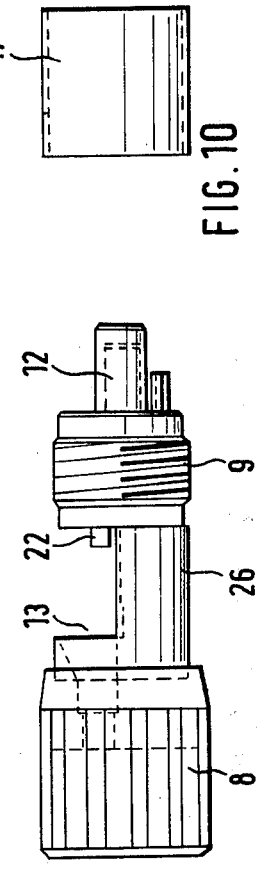
FIG. 9 illustrates a side view of the intermediate member pursuant to FIGS. 1, 2 and 4 in an enlarged scale, however, without the cylindrical socket containing the electrical connecting wires and contact.
Figure 12:
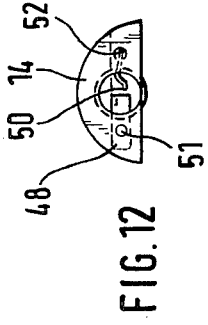
FIG. 12 illustrates a right-hand end view of the socket pursuant to FIG. 11.

Approximately in the middle of the body 26 of the cylindrical intermediate member 6, the latter is provided with a cutout 13, as can be ascertained particularly from FIG. 9, which in contacting all sides in the recess 13, and ending closely fitted with the cylindrical surface of the intermediate member 6, is a cylindrical section forming socket 14 of an electrical lightbulb 15, refer herein to FIGS. 11 through 14. The lightbulb 15 which projects from an end surface of the socket 14, during the building-in of the socket 14 is insertable into the cutout 13 of the intermediate member 6 in a through-bore 16 thereof. The lightbulb 15 and the through-bore 16 which is associated therewith are hereby so axially oriented that precisely therewith, axially alike, the rearward end of the strand-like light conductor 5 will fit into the opening of the mentioned bore 16 which is towards the worktool end, and extend into close proximity with the lightbulb.

The retention of the socket 14 in the recess 13 is hereby effected alone by a sleeve 17 constituted of an insulating material, which is slid out from the end of the intermediate member 16 at the hose over the intermediate member 6, and upon the building-in thereof, is retained by the cap nut 8 with clamping engagement.

As can be ascertained from FIGS. 6, 8, 20 and 21, arranged in the rearward end of the intermediate member 6, proximate the media conduits 18 and axially parallel therewith, is a pneumatic switch arrangement 19, which consists of a pneumatic cylinder 20-piston 21 unit, coaxially with the lightbulb 15. It consists of a cylinder 20 which is formed by a bore through the intermediate member body 26 and a piston 21 located therein, the latter of which is pressed by means of a coil spring 23 arranged about a push rod 22 towards the hose-end of the intermediate member 6. The cylinder 20 is closed off at its rearward end by means of a threaded closure 24. In order to seal the piston 21 with respect to the wall of the cylinder 20, arranged about the periphery of the piston 21 within an annular groove is a sealing ring 25. Fastened on the free end surface of the push rod 22 is a disc 53 of insulating material.

The operating chamber of the cylinder 20 stands in connection with the conduit 18 conveying the operating air for the drive aggregate through a bypass conduit 27, which is closed off with respect to the operating air conduit 18 by means of a non-return ball valve 28. The non-return ball valve 28 hereby consists of a ball 29 with a compression coil spring 30 which, on the one end supports itself on a snap ring which is inserted in a groove in the bypass conduit 27 and, on the other end, presses the ball 29 against a restriction 31 acting as a valve seat at the inlet of the bypass conduit 27. The bore 33 in the intermediate member 6 required for the formation of the bypass conduit 27 facing towards the cylinder 20 is closed off by means of a ball 34. In case that no compressed air-driven drive aggregate is provided but, for example, an electric motor, the conduit may, for instance, be a cooling air conduit leading to the dental treatment worktool.

In order, upon switching off of the operating air for the drive aggregate or, respectively, cooling air for the worktool, to achieve a delayed reduction in the pressure in the operating chamber of the cylinder 20, in conjunction with the non-return ball valve 28 there is provided an adjustable throttle valve 35 which after the sudden closing of the non-return ball valve 28, facilitates a gradual outflow of the compressed air contained in the cylinder 20. This has the result that the operating condition of the light source remains maintained for a predetermined period as would be for a type of a nightlamp.

The throttle valve 35 hereby consists of a threaded pin 36 provided with a conical tip 37 and which can be manipulated from the exterior, which can be threaded into a first tie conduit 38 in the direction of the cylinder 20, and by means of which there is formed the throttling location at the crossing of the first tie conduit 38 with a second tie conduit 39.

The above described pneumatic switch device 19, which consists of a pneumatic cylinder-piston unit, acts for instance with its piston 21, in effect with its pusher rod 22, on the electrical switch arrangement 40 which is described in greater detail hereinbelow for the six embodiments illustrated in FIGS. 1 through 7, 11 through 19, and 23 through 27.

In the first embodiment of the electrical switch arrangement 40 which can be recognized particularly from FIGS. 6, 7 and 11 through 14, projecting sideways into a rear cutout 47 in the socket 14, is a contact spring 48 which is retained in the socket 14, which is located at a distance from a contact plate 49 of the lighbulb 15 and to which there is fastened or, for example, soldered, an electrical contact wire 51 extending from the front of socket 14 rearwardly. Moreover, the other electrical conductor wire 52 passes through socket 14 rearwardly from the front, however, it is directly fastened or, soldered to the other contact plate 50 of the lightbulb 15.

As is ascertainable from FIG. 7, the free end of the contact spring 48 which freely projects into the socket recess 47 is so dimensioned that upon the sliding forward of the piston 21 under the action of the compressed air, the pusher rod 22 which is provided with an insulating plate 53 will press the contact spring 48 against only the one contact plate 49 of the lightbulb, while the other contact plate 50 will remain completely unaffected. During the pressing of the contact spring 48 against the contact plate 50, the electrical current circuit is closed, and the lightbulb is in operation.

In the second embodiment of the electrical switch arrangement 41 as illustrated in FIGS. 2, 3, 15 and 16, the two conductor wires 51 and 52 terminate in a contact head 54 which is insertable into an elbow-shaped plug contact 55. The exposed ends of the conductor wires 51 and 52 are connected through connector pins 56 and 57 which are inserted into the plug contact 55 with the poled pins 58 and 59 of the plug contact 55 which, in turn, are insertable into sleeves 60 and 61 of the lightbulb socket 14. Fastened, in turn, on these sleeves 60 and 61 are the contact springs 62 and 63, for example, soldered thereto, which are retained in the socket 14 and are secured downwardly through an insulating bar 65. The contact spring 62, which is illustrated at the left side of FIG. 16, hereby corresponds to the contact spring 48 described in the first embodiment of the electrical switch arrangement 40, and freely projects into the socket cutout 47 into the height of the one contact plate 49 of the lightbulb. The other contact spring 63 is fixedly connected by means of a wire section 64 with the other contact plate 50 of the lightbulb 15.

The third embodiment of the electrical switch arrangement 42, with respect to the contact springs 62 and 63, and the contact head 54, is the same as that of the second embodiment. The only distinction lies in the conductance of the electrical current to the contact springs 62 and 63. Here, in essence, the contact head 54, as can be ascertained from FIGS. 17 through 19, is inserted in an upper expansion 66 of the sleeve 17 which is slideable onto the intermediate member 6, and the electrical connection to the contact springs 62 and 63 is produced in that, at the contact locations 69 and 70 of the contact head 54, connector pins 71 and 72 which are built-in horizontally in the expansion 66 stand in connection, through vertical connector pins 73 and 74 arranged perpendicularly at their ends, with loop contact bars 75 and 76 which are arranged in the surface of the lightbulb socket 14. Formed between these loop contact bars 75 and 76 and the contact springs 62 and 63, is a fixed connection by means of connector pins 79 and 80 passing through the socket 14. The manner of operation of this switch arrangement 42 is, for the remainder, the same as that of the switch arrangement 41.

For the special construction of the contact springs 62 and 63 illustrated in FIG. 23 for the fourth embodiment of the electrical switch arrangement 43, the supply of the electrical current to the contact springs 62 and 63 is the same as that in the second embodiment of the electrical switch arrangement 41 as illustrated in FIGS. 15 and 16. Only the contract spring 63 which is shown towards the right side in FIG. 16 is now constructed to be as long as the left side contact spring 62 and is not connected with the contact plate 50 through a short wire piece 64. The differently shaped contact spring 81 also passes over the contact plate 50 at a spacing therewith, and the pusher rod 22 of the pneumatic switch device 19 during its pressing sequence engages both free ends of the contact springs 62 and 81 and presses these against the contact plates 49 and 50 of the lightbulb 15.

Also in the special construction illustrated in FIG. 24, the current supply to the contact plates 49 and 50 of the lightbulb 15, for the fifth embodiment of the electrical switch arrangement 44 the conductance of the electrical current from the contact head 54 through the base 14 is the same as for the second embodiment illustrated in FIGS. 15 and 16. However, different herein is the connection between the sleeves 60 and 61 and the contact plates 49 and 50 of the lightbulb. In this instance, there the one sleeve 61 is thus connected by means of a wire piece 83 with the contact plate 50 of the lightbulb 15, while the other sleeve 60 is also brought into connection, by means of a wire piece 84, with a headpiece 85 which conducts the electrical current at the end surface of the pusher rod 22.

Upon actuation of the pneumatic switch arrangement 19, the headpiece 85 of the pusher rod 22 is pressed against the contact plate 49, and thereby the electrical current circuit is closed.

The coil spring 23 which presses the piston 21 towards the end of the intermediate member 6 adjacent the hose can be eliminated when, as illustrated in FIG. 25, the contact spring 86 is suitably bent and is correspondingly proportioned in its spring force.

For the above-described five embodiments of the electrical switch arrangements 40 through 44 it is necessary that the electrical contact wires 51 and 52 lead to the exterior of the supply hose 11 to the intermediate member 6, in view of which there are required a plurality of clips 87. Externally located conductor wires of that type, however, during use of the dental handpiece have been found as to be quite disruptive. In order to improve upon the foregoing, by means of a sixth embodiment of the electrical switch arrangement, there is proposed that for the energy source required for the operation of the lightbulb 15 be provided so as to be no longer so far removed from the dental handpiece 1, but that it be located within the intermediate member 6 of the dental handpiece 1, to thereby eliminate any kind of lengthy electrical conductor wires externally and internally of the dental handpiece.

Figure 26:
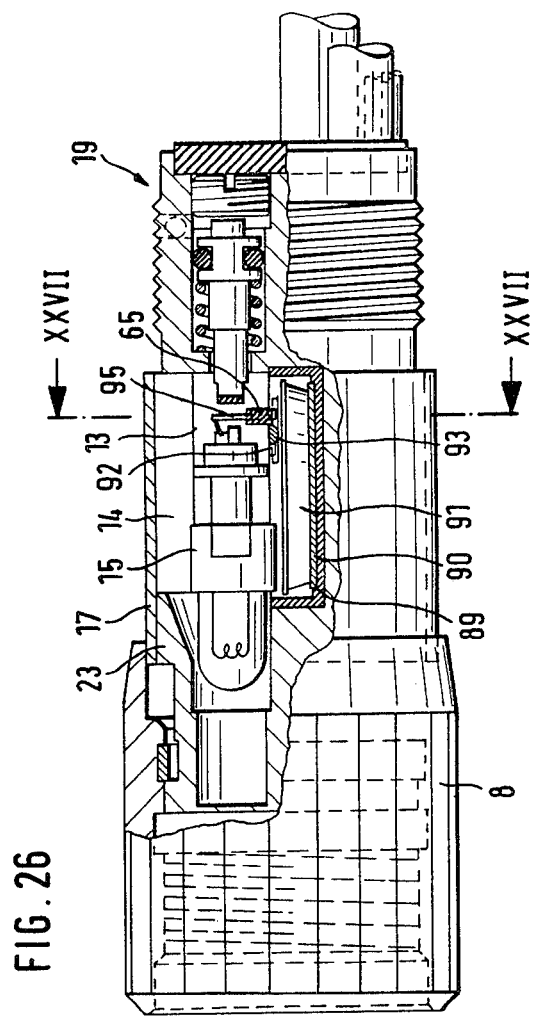
FIG. 26 illustrates, in an enlarged scale partially sectional side view, the intermediate member pursuant to FIG. 15, with a sixth embodiment of the electrical current connector.
Figure 27:
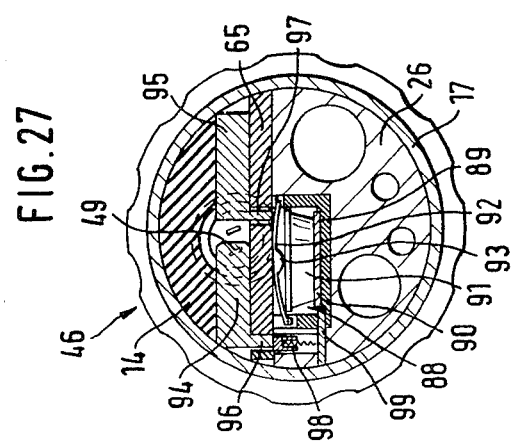
FIG. 27 illustrates a section taken along line XXVII—XXVII in FIG. 26.

For this purpose, as can be ascertained from FIGS. 26 and 27, there is provided, below the electrical lightbulb 15 and its connector components in the body 26 of the intermediate member 6, a further cutout 88 into which there is introduced a flat insulating trough 89. On a plate 90 which is formed of electrically current conductive material which is arranged on the bottom of the trough 89 there is mountable a miniature battery 91. Over the length of the insulating trough 89 there is clamped an elbow 92 which, by means of a central contact head 93, contacts the surface of the miniature battery 91.

At the elevation of the electrically-conductive base plate 90, a bore is located in the body 26 of the intermediate member 6 and in the wall of the insulating trough 89, into which there is inserted a contact pin 99. Inserted over the entire width of the cutout 13 is an insulating bar 65 on which there lie the contact springs 94 and 95 which are retained in the socket 14, each having a projection 96, 97 passing through this insulating bar 65. The projection 96 of the contact spring 94 at its other end which freely extends into cutout 13 of the socket 6, hereby contacts a coil spring contact 98 which is located in a perpendicular bore in the bottom of the cutout 13, which spring at its lower end contacts against the contact pin 99. The projection 97 of the other contact spring 95 lies on the clamping elbow 94 which conducts the electrical current. When, during actuation of the pneumatic switch device 19, the pusher rod 22 is pressed against the free end of the contact spring 94, this will touch the contact plate 49 of the lightbulb 15, and the lightbulb will emanate light.

The exchange of a used miniature battery with a new one is rendered possible, in a simple manner, in that the sleeve 17 on the intermediate member 6 is slid back towards the supply hose 11, the socket 14 together with the lightbulb 15 is removed from the cutout 13 and the clamping elbow 92 is bent aside whereupon the miniature battery 91 can be effortlessly removed from the insulating trough 89. Just as easily can there be carried out the insertion of a new miniature battery.

While there has been shown and described what are considered to be preferred embodiments of the invention, it should be understood that variations in form and detail could readily be made without departing from the spirit of the invention. It is therefore intended that the invention be not limited to the exact form and detail shown herein and described, nor to anything other than the whole of the invention as hereinafter claimed.

What is claimed:

1. In a dental handpiece including a gripping sleeve; a drive aggregate arranged within said handpiece for a dental treatment worktool retained in a head portion; a built-in electrical light source for said handpiece; an intermediate member for said light source and conduits for supply media, said intermediate member being interchangeably arranged between the gripping sleeve and the end member of a supply hose for the supply media for the handpiece, the light of said light source being conducted to the region of the handpiece head portion through a strand-like light conductor arranged interiorly of said handpiece and extending from said gripping sleeve while being directed at said head portion onto the dental treatment tool; and compressed air-actuated pneumatic switch means for activating and deactivating said light source; the improvement comprising in that said cylindrical intermediate member contains said light source and said pneumatic switch means.

2. Handpiece as claimed in claim 1, comprising a cutout formed in the central portion of said intermediate member, said cutout and the cylindrical surface of the intermediate member being fitted so as to seal off a cylindrically-shaped socket for an electrical lightbulb formed by said light source, said lightbulb projecting beyond said socket towards the side of the worktool and being freely insertable through an axial bore formed in said intermediate member.

3. Handpiece as claimed in claim 1 or 2, said socket being formed of an insulating material, such as plastic, and electrical conductor wires and contacts being contained within said socket.

4. Handpiece as claimed in claim 3, comprising a sleeve of an insulating material being slideable onto said intermediate member to cover said central cutout.

5. Handpiece as claimed in claim 1 or 2, said pneumatic switch means comprising a pneumatic cylinder-piston or cylinder-membrane unit suppliable from one of said supply media through a bypass conduit from the compressed air-actuated means to act on a contact spring resiliently arranged on the socket of said electrical lightbulb, the free end of said contact spring being located at a distance from a plate on the lightbulb.

6. Handpiece as claimed in claim 5, said pneumatic cylinder-piston unit or said pneumatic cylinder-membrane unit being arranged in said intermediate member in an axial extension of the lightbulb facing towards the media supply hose.

7. Handpiece as claimed in claim 5, said pneumatic cylinder-piston unit or said pneumatic cylinder-membrane unit being arranged in said intermediate member in an axial extension of the lightbulb facing towards the media supply hose.

8. Handpiece as claimed in claim 7, comprising a non-return ball valve located at the inlet to said bypass conduit and normally retained in a closed position by a pressure spring, said cylinder communicating with the exterior through a separate tie conduit; and a throttle valve being arranged in said tie conduit.

9. Handpiece as claimed in claim 8, said throttle valve comprising an externally-operable threaded pin having a conical tip.

10. Handpiece as claimed in claim 4, comprising two electrical conductor wires traversing said socket from forwardly towards the rear thereof, one said electrical wire being fastened to one contact plate of said lightbulb and the other wire being fastened to a contact spring, said contact spring projecting freely into a cutout in said lightbulb socket and being adapted to be resiliently pressed at its free end by the pneumatic switch means against a second contact plate on said lightbulb.

11. Handpiece as claimed in claim 4, the end of said two electrical conductor wires being combined at a spacing from each other within a contact head, said contact head being insertable into an elbow-shaped plug contact having two pole pins insertable into sleeves of the lightbulb socket, said pole pins each being respectively connected with a contact spring, one said spring being fastened to one contact plate of said lightbulb and the other spring having its free projecting end resiliently pressable into a cutout in the lightbulb socket by the pneumatic switch means against a second contact plate on said lightbulb.

12. Handpiece as claimed in claim 4, when said sleeve is slidable onto said intermediate member and comprises an upper widening, the ends of said electrical conductor wires combined in said contact head being inserted into said sleeve to form a connection in said widening through contact connector pins with loop contact bars inserted axially in the surface of said lightbulb socket, further pole pins being fixed on said loop contact bars extending through the lightbulb socket and being fastened at the other end to contact springs, on said pole pin being fastened to one contact plate of the lightbulb and the other pole pin being fastened to another contact plate on the lightbulb being pressed thereagainst with its end freely extending into the cutout of the lightbulb socket responsive to pressure from the pneumatic switch means.

13. Handpiece as claimed in claim 4, the ends of said two electrical conductor wires being combined within a contact head which is inserted into an elbow-shaped contact, two pole pins being insertable into sleeves of the lightbulb socket, said sleeves each being respectively connected with a contact spring having both of the ends thereof projecting into a cutout of the lightbulb socket and resiliently pressed by the pneumatic switch means against the contact plates on said lightbulb.

14. Handpiece as claimed in claim 4, the ends of said two electrical conductor wires being combined within a contact head inserted into an elbow-shaped plug contact, two pole pins being insertable into sleeves of the lightbulb socket, one said sleeve being connected through a wire with one contact plate of the lightbulb and the other sleeve through the wire with a conductive headpiece on the piston of said pneumatic switch means.

15. Handpiece as claimed in claim 3, said conductor wires leading to the intermediate member being fastened by clips on a media hose.

16. Handpiece as claimed in claim 1, said intermediate member having a cap screw at its connecting end towards the handpiece for connection to the gripping sleeve, and an external threading at its hose end for connection to the end member of the supply hose.

17. Handpiece as claimed in claim 1, comprising a miniature battery within said intermediate member, said battery being connectable to switch contacts for the lightbulb actuatable by said pneumatic switch means.

18. Handpiece as claimed in claim 17, said miniature battery being arranged interchangeably in the bottom of said central cutout of said intermediate member and being conductably contacted by contact springs which act on the contact plates on said lightbulb.

* * * * *